United States Patent
Akagane (10) Patent No.: US 11,491,511 B2
(45) Date of Patent: Nov. 8, 2022

(54) VIBRATION TRANSMITTING MEMBER, ULTRASONIC TREATMENT INSTRUMENT AND VIBRATING BODY UNIT

(71) Applicant: OLYMPUS CORPORATION, Hachioji (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 1149 days.

(21) Appl. No.: 16/037,248

(22) Filed: Jul. 17, 2018

(65) Prior Publication Data
US 2018/0318878 A1 Nov. 8, 2018

Related U.S. Application Data

(63) Continuation of application No. PCT/JP2016/051433, filed on Jan. 19, 2016.

(51) Int. Cl.
*A61N 7/00* (2006.01)
*B06B 3/00* (2006.01)
(Continued)

(52) U.S. Cl.
CPC ................ *B06B 3/00* (2013.01); *A61B 17/29* (2013.01); *A61B 17/320092* (2013.01);
(Continued)

(58) Field of Classification Search
CPC ............ A61B 17/29; A61B 17/320092; B06B 1/0611; B06B 2201/76
See application file for complete search history.

(56) References Cited

U.S. PATENT DOCUMENTS

| | | |
|---|---|---|
| 5,989,275 A | 11/1999 | Estabrook et al. |
| 2006/0090956 A1 | 5/2006 | Peshkovskiy et al. |

(Continued)

FOREIGN PATENT DOCUMENTS

| | | |
|---|---|---|
| JP | S58-171321 U | 11/1983 |
| JP | H07-255736 A | 10/1995 |

(Continued)

OTHER PUBLICATIONS

Aug. 19, 2019 Search Report issued in European Patent Application No. 16886274.6.

(Continued)

*Primary Examiner* — Muhammad S Islam
(74) *Attorney, Agent, or Firm* — Oliff PLC (57) ABSTRACT

A vibration transmitting member transmits ultrasonic vibration generated by an ultrasonic transducer from a proximal side toward a distal side. The vibration transmitting member includes a connection connected to the ultrasonic transducer. When a reference vibration node, which is located most proximally among vibration nodes occurring on the distal side relative to the connection, is defined, while the vibration transmitting member vibrates at a resonance frequency in a predetermined frequency range, a cross-sectional area decreasing part is provided between the connection and the reference vibration node. In the cross-sectional area decreasing part, a cross-sectional area perpendicular to a longitudinal direction gradually decreases from the distal side toward the proximal side.

10 Claims, 2 Drawing Sheets

(51) Int. Cl.
  *B06B 1/06* (2006.01)
  *A61B 17/29* (2006.01)
  *A61B 17/32* (2006.01)

(52) U.S. Cl.
  CPC .............. *B06B 1/06* (2013.01); *B06B 1/0611* (2013.01); *B06B 2201/76* (2013.01)

(56) References Cited

U.S. PATENT DOCUMENTS

| | | |
|---|---|---|
| 2013/0274637 A1 | 10/2013 | Akagane |
| 2014/0222052 A1 | 8/2014 | Stoddard et al. |
| 2015/0080927 A1 | 3/2015 | Akagane |
| 2016/0030076 A1* | 2/2016 | Faller ............. A61B 17/320092 606/169 |
| 2018/0146975 A1* | 5/2018 | Zhang ..................... A61N 7/00 |

FOREIGN PATENT DOCUMENTS

| | | |
|---|---|---|
| JP | 2002-58679 A | 2/2002 |
| JP | 2002-542005 A | 12/2002 |
| JP | 2008-236781 A | 10/2008 |

OTHER PUBLICATIONS

Apr. 26, 2016 International Search Report issued in International Patent Application No. PCT/JP2017/051433.
Jun. 14, 2019 Office Action issued in Chinese Patent Application No. 2016800794094.
Nov. 5, 2020 Office Action issued in European Patent Application No. 16886274.6.

* cited by examiner

VIBRATION TRANSMITTING MEMBER, ULTRASONIC TREATMENT INSTRUMENT AND VIBRATING BODY UNIT

CROSS-REFERENCE TO RELATED APPLICATIONS

This is a Continuation Application of PCT Application No. PCT/JP2016/051433, filed Jan. 19, 2016, the entire contents of which are incorporated herein by reference.

BACKGROUND OF THE INVENTION

1. Field of the Invention

The present invention relates to a vibration transmitting member which transmits ultrasonic vibration. The invention also relates to an ultrasonic treatment instrument and a vibrating body unit, each including the vibration transmitting member.

2. Description of the Related Art

U.S. Patent Application Publication No. 2013/0274637 discloses an ultrasonic treatment instrument including a vibration transmitting member which transmits ultrasonic vibration generated by an ultrasonic transducer. In this ultrasonic treatment instrument, an energy applying portion is formed in a distal portion of the vibration transmitting member. The ultrasonic vibration transmitted through the vibration transmitting member is applied from the energy applying portion to a treated target which is grasped between the energy applying portion and a grasping member. In addition, the above-described patent document 1 discloses a configuration in which none of vibration anti-nodes is located at a connection position between the ultrasonic transducer and vibration transmitting member in a state in which a vibrating body unit, which is formed by the ultrasonic transducer and vibration transmitting member, vibrates at any one of resonance frequencies in a predetermined frequency range. By this configuration, the ultrasonic transducer, to which the vibration transmitting member is not connected, is prevented from vibrating as a single piece.

BRIEF SUMMARY OF THE INVENTION

According to one aspect of the invention, a vibration transmitting member attached to an ultrasonic transducer, the vibration transmitting member being configured to transmit ultrasonic vibration, which is generated by the ultrasonic transducer, from a proximal side toward a distal side, thereby vibrating at a resonance frequency in a predetermined frequency range, the vibration transmitting member including: a connection connected to the ultrasonic transducer; and a cross-sectional area decreasing part provided between the connection and a reference vibration node in a longitudinal direction, the reference vibration node being defined as being located most proximally among vibration nodes occurring on the distal side with respect to the connection in a state in which the vibration transmitting member vibrates at the resonance frequency, the cross-sectional area decreasing part having such a cross-sectional area perpendicular to the longitudinal direction as to gradually decrease from the distal side toward the proximal side.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION (First Embodiment)

Figure 1:
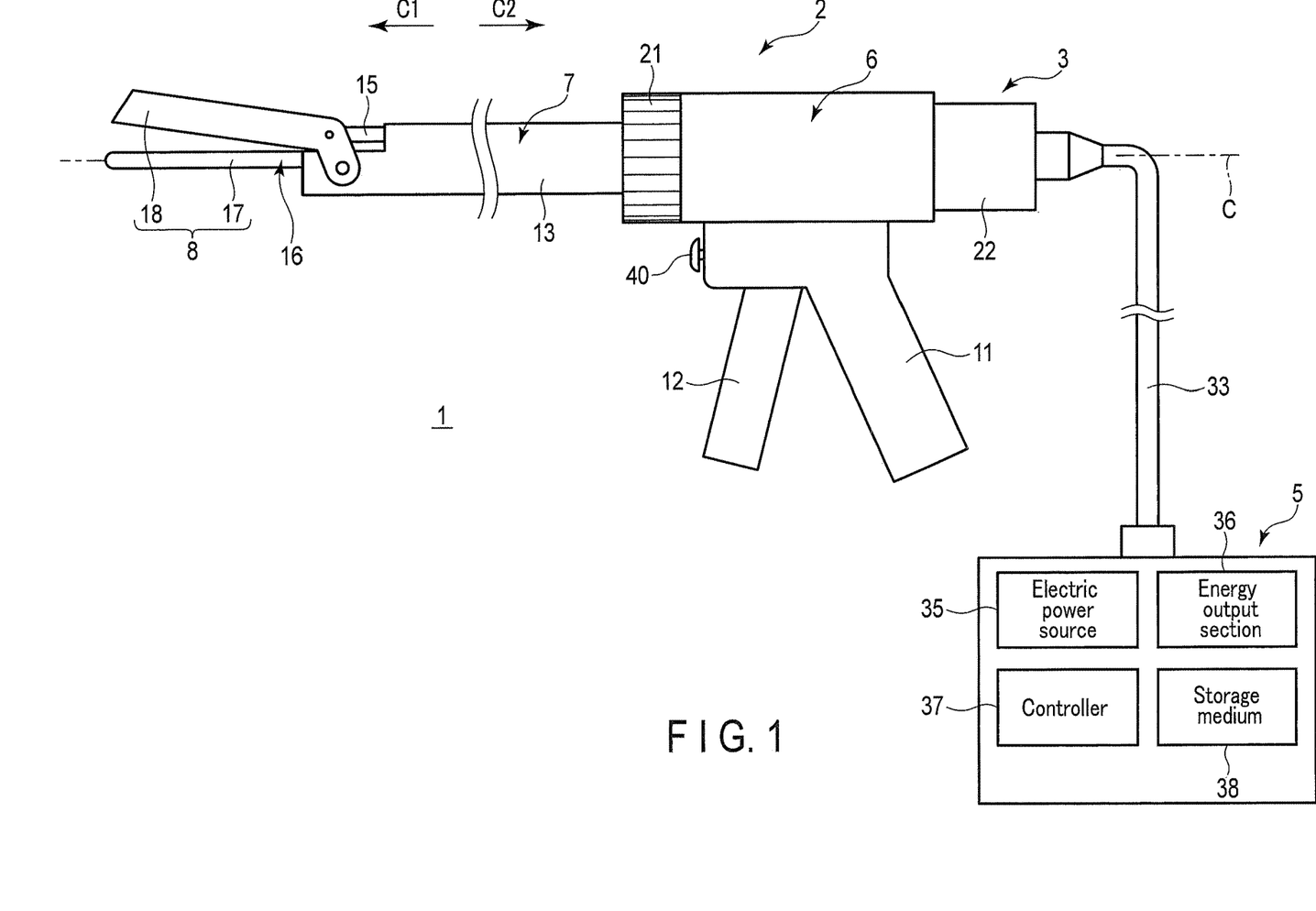
FIG. 1 is a schematic view illustrating a treatment system according to a first embodiment.

A first embodiment of the present invention is described with reference to FIG. 1 to FIG. 3. FIG. 1 is a view illustrating a treatment system 1 of the present embodiment. As illustrated in FIG. 1, the treatment system 1 includes an ultrasonic treatment instrument 2, a transducer unit 3 and an energy control device 5. The ultrasonic treatment instrument 2 has a longitudinal axis C. Here, a direction along the longitudinal axis C is defined as a longitudinal direction (directions indicated by arrow C1 and arrow C2). In addition, one side of the longitudinal direction is a distal side (arrow C1 side), and an opposite side to the distal side is a proximal side (arrow C2 side).

The ultrasonic treatment instrument 2 includes a housing 6 which can be held, a shaft portion (shaft) 7 which is coupled to the housing 6 from the distal side, and an end effector 8 provided in a distal portion of the shaft portion 7. The housing 6 includes a grip (stationary handle) 11 which extends along a direction crossing the longitudinal axis C. In addition, a handle (movable handle) 12 is rotatably attached to the housing 6. By the handle 12 rotating relative to the housing 6, the handle 12 opens or closes relative to the grip 11.

The shaft portion 7 includes a cylindrical sheath 13 which forms an exterior, and a movable portion 15 which extends in the inside of the sheath 13. Each of the sheath 13 and movable portion 15 extends along the longitudinal axis C (longitudinal direction). For example, the center axis of the sheath 13 is substantially coaxial with the longitudinal axis C. In the inside of the housing 6, the handle 12 is coupled to a proximal portion of the movable portion 15. By the handle 12 opening or closing relative to the grip 11, the movable portion 15 moves relative to the housing 6 and sheath 13 in the longitudinal direction (along the longitudinal axis C).

A vibration transmitting member (ultrasonic probe) 16 extends from the inside of the housing 6 toward the distal side. The vibration transmitting member 16 is formed of a material with high vibration transmissibility such as Ti-6A1-4V or duralumin. In addition, the vibration transmitting member 16 is inserted through the shaft portion 7, and extends along the longitudinal axis C through the inside of the shaft portion 7 (sheath 13 and movable portion 15). An energy applying portion (probe treatment section) 17 is formed in a distal portion of the vibration transmitting member 16. The energy applying portion (first grasping piece) 17 projects from the distal end of the shaft portion 7 toward the distal side.

A grasping member (jaw) 18 is rotatably attached to a distal portion of the sheath 13. In addition, a distal portion of the movable portion (movable pipe) 15 is connected to the grasping member (second grasping piece) 18. By the movable portion 15 moving along the longitudinal axis C in accordance with the movement of the handle 12, the grasping member 18 rotates, and the energy applying portion (energy applier) 17 and grasping member 18 open or close relative to each other. In the present embodiment, the end effector 8 is composed of the energy applying portion 17 and grasping member 18. By the energy applying portion 17 and grasping member 18 closing relative to each other, a treated target such as a biological tissue can be grasped between the energy applying portion 17 and grasping member 18.

In addition, a rotation knob 21 is attached to the housing 6, and the rotation knob 21 is fixed to the sheath 13. By rotating the sheath 13 around the longitudinal axis C relative to the housing 6, the shaft portion 7, end effector 8 and vibration transmitting member 16 rotate together around the longitudinal axis C relative to the housing 6.

The transducer unit 3 is coupled to the housing 6 from the proximal side. FIG. 2 is a view illustrating the configuration of the transducer unit 3 and vibration transmitting member 16. As illustrated in FIG. 1 and FIG. 2, the transducer unit 3 includes a transducer case 22, and an ultrasonic transducer 23 which is disposed in the inside of the transducer case 22. In the inside of the housing 6, the transducer case 22 is attached to the shaft portion 7 from the proximal side. The ultrasonic transducer 23 includes a relay member 25, piezoelectric elements 26 (three piezoelectric elements 26 in this embodiment) which are attached to the relay member 25, and electrode members 27A and 27B which are attached to the relay member 25. Each of the piezoelectric elements 26 is interposed between the electrode members 27A and 27B.

In the inside of the housing 6, the relay member 25 is connected to the vibration transmitting member 16 from the proximal side, and the ultrasonic transducer 23 is attached to the vibration transmitting member 16 from the proximal side. Thereby, a vibrating body unit 10 is formed by the vibration transmitting member 16 and ultrasonic transducer 23. In this embodiment, in the vibrating body unit 10, in the state in which the ultrasonic transducer 23 is attached to the vibration transmitting member 16, an abutment surface 31B of the vibration transmitting member 16 abuts on a distal surface 31A of the ultrasonic transducer 23 (relay member 25). In addition, in this embodiment, in the ultrasonic transducer 23, an engaging groove 32A, which is recessed toward the proximal side from the distal surface 31A, is formed. In the vibration transmitting member 16, an engaging projection 32B, which projects toward the proximal side from the abutment surface 31B, is formed. By the engaging projection 32B being engaged in the engaging groove 32A, the vibration transmitting member 16 is connected to the ultrasonic transducer 23. In the above-described configuration, the abutment surface 31B, which is provided in the proximal portion of the vibration transmitting member, is a connection portion which is connected to the ultrasonic transducer 23. In addition, an abutment position between the distal surface 31A and abutment surface 31B becomes a connection position B0 between the ultrasonic transducer 23 and vibration transmitting member 16.

One end of a cable 33 is connected to the transducer unit 3, and the other end of the cable 33 is detachably connected to the energy control device 5. The energy control device 5 includes an electric power source 35 such as a battery or a plug socket, an energy output section (energy output source) 36 including a converter circuit, etc., a controller 37 such as a processor or an integrated circuit including a CPU (Central Processing Unit) or an ASIC (application specific integrated circuit), and a storage medium 38. The energy output section 36 is electrically connected to the ultrasonic transducer 23 via electric wiring (not shown) or the like provided in the inside of the cable 33. In addition, an operation button 40 functioning as an energy operation input portion is attached to the housing 6. In the treatment system 1, for example, a signal path (not shown) is formed through the inside of the transducer unit 3 and cable 33. Based on operation signals, etc., which are transmitted through the signal path, the controller 37 judges whether an operation input is being performed by the operation button 40 or not.

Based on the detection of an operation input by the operation button 40, the controller 37 drives the energy output section 36. Thereby, the energy output section 36 converts electric power from the electric power source 35 to, for example, AC electric power of a predetermined frequency, and outputs the converted electric energy. Then, by the electric energy being supplied from the energy output section 36 to the ultrasonic transducer 23, a voltage (e.g. an AC voltage of a predetermined frequency) is applied between the electrode members 27 and 28. Thereby, each of the piezoelectric elements 26 converts the current (e.g. an AC current of a predetermined frequency) to ultrasonic vibration, and ultrasonic vibration is generated by the ultrasonic transducer 23.

The ultrasonic vibration generated by the ultrasonic transducer 23 is transmitted to the vibration transmitting member 16 through the distal surface 31A of the ultrasonic transducer 23 and the abutment surface 31B of the vibration transmitting member 16. Then, in the vibration transmitting member 16, the ultrasonic vibration is transmitted to the energy applying portion 17 from the proximal side toward the distal side. The energy applying portion 17 applies the transmitted ultrasonic vibration to a treated target grasped between the energy applying portion 17 and grasping member 18, thereby treating the treated target by using the ultrasonic vibration. In this embodiment, by the vibration transmitting member 16 transmitting the ultrasonic vibration, the vibrating body unit 10 including the vibration transmitting member 16 vibrates (resonates) at any one of resonance frequencies in a predetermined frequency range. At this time, the vibrating body unit 10 performs longitudinal vibration having a vibration direction which is substantially parallel to the longitudinal direction (longitudinal axis C). In one example, the vibrating body unit 10 is designed in such a state that the vibrating body unit 10 vibrates at 47 kHz, and actually vibrates at any one of frequencies in a range of between 46 kHz and 48 kHz, preferably between 46.5 kHz and 47.5 kHz.

In the present embodiment, the vibrating body unit 10 vibrates at any one of the resonance frequencies in the predetermined frequency range. Thereby, a plurality of vibration anti-nodes $A_i$ (i=0, k, k+1) and a plurality of vibration nodes $N_j$ (j=0, k) occur in the vibration transmitting member 16. At this time, a vibration anti-node $A_0$ is located at the proximal end of the ultrasonic transducer 23 (at the proximal end of the vibrating body unit 10), and a vibration anti-node Ak+1 is located at the distal end of the vibration transmitting member 16 (at the distal end of the vibrating body unit 10). It is assumed that, of the vibration anti-nodes Ai, the vibration anti-node A0 is located most proximally, and the vibration anti-node Ak+1 is located most distally. In addition, the natural number i of the vibration anti-node Ai increases one by one toward the distal side. Similarly, it is assumed that, of the vibration nodes Nj, a vibration node N0 is located most proximally, and a vibration node Nk is located most distally. In addition, the natural number j of the vibration node Nj increases one by one toward the distal side. Besides, each of the vibration nodes Nj occurs at a half-wavelength portion between the vibration anti-node (corresponding Aj) and the vibration node (corresponding Aj+1). For example, the vibration node N0 occurs between the vibration anti-nodes A0 and A1, and the vibration node N1 occurs between the vibration anti-nodes A1 and A2.

Figure 2:
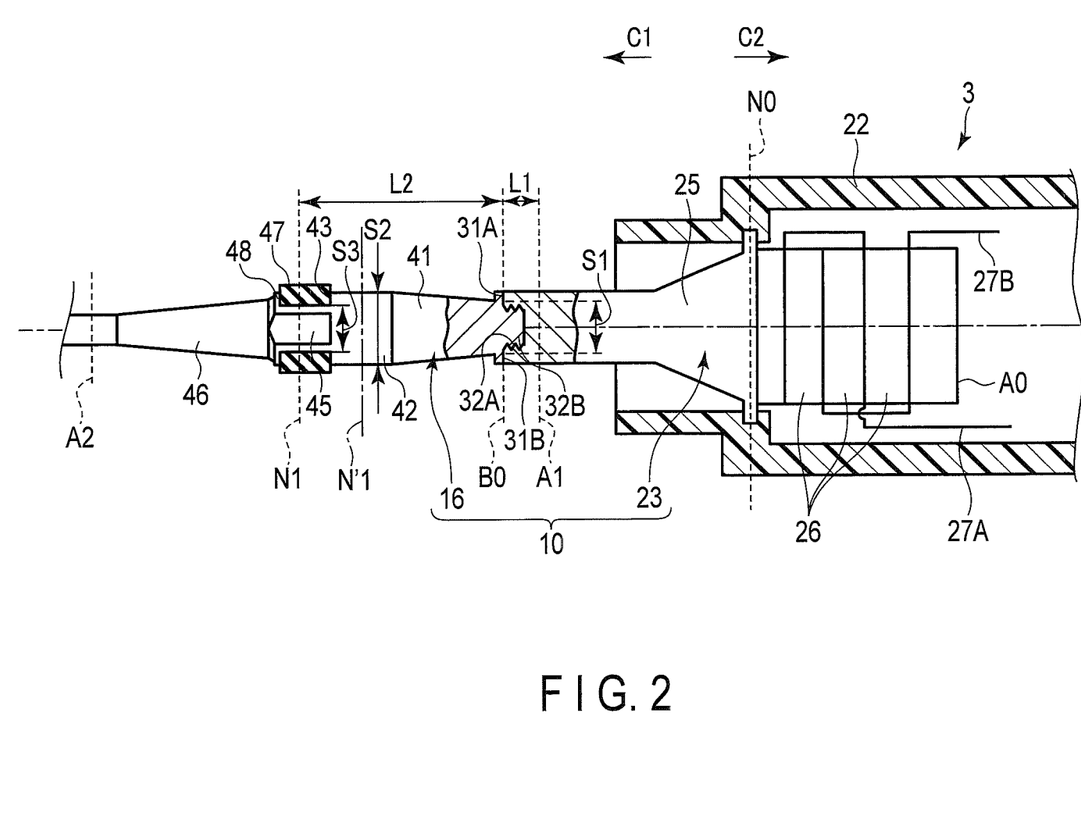
FIG. 2 is a schematic view illustrating a configuration of a transducer unit and a vibration transmitting member according to the first embodiment.
Figure 3:
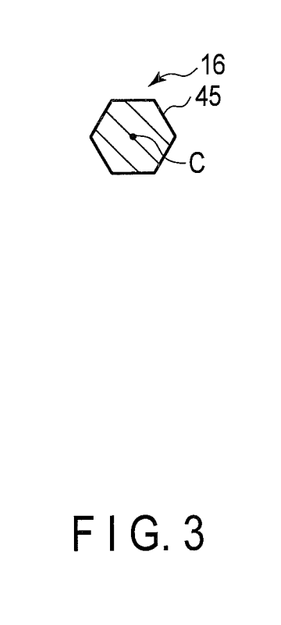
FIG. 3 is a cross-sectional view which schematically illustrates a supported portion of the vibration transmitting member according to the first embodiment by a cross section substantially perpendicular to a longitudinal direction.

As illustrated in FIG. 2, the vibration transmitting member 16 is provided with a taper portion 41 and a supported portion 45 on the distal side with respect to the abutment surface (connection portion) 31B. The taper portion 41 is provided between the abutment surface 31B (connection position B0) and the supported portion 45 in the longitudinal direction. In the taper portion 41, the cross-sectional area substantially perpendicular to the longitudinal direction gradually decreases from the distal side toward the proximal side. Thus, at the proximal end of the taper portion 41, the cross-sectional area substantially perpendicular to the longitudinal direction becomes a cross-sectional area S1. On the other hand, at the distal end of the taper portion 41, the cross-sectional area substantially perpendicular to the longitudinal direction becomes a cross-sectional area (maximum cross-sectional area) S2 which is greater than the cross-sectional area S1. Note that in the present embodiment, in the taper portion 41, the cross-sectional shape substantially perpendicular to the longitudinal direction is circular.

In addition, a maximum-diameter portion 42 extends from the distal end of the taper portion 41 toward the distal side. In this embodiment, in the maximum-diameter portion 42, the cross-sectional shape substantially perpendicular to the longitudinal direction is circular. Besides, in the vibration transmitting member 16, the outside diameter becomes a maximum outside diameter in the maximum-diameter portion 42. Furthermore, in the vibration transmitting member 16, the cross-sectional area substantially perpendicular to the longitudinal direction becomes the maximum cross-sectional area S2 in the maximum-diameter portion 42. The maximum-diameter portion 42 is provided between the taper portion 41 and supported portion 45 in the longitudinal direction. In this embodiment, the maximum-diameter portion 42 is continuous from the distal end of the taper portion 41 to the proximal end of the supported portion 45. In the maximum-diameter portion 42, the outside diameter is substantially uniform at the maximum outside diameter over the entire length from the proximal end to distal end in the longitudinal direction, and the cross-sectional area substantially perpendicular to the longitudinal direction is substantially uniform at the maximum cross-sectional area S2.

The supported portion 45 is formed in a groove shape, which is recessed toward the inner peripheral side over the entire circumference around the longitudinal axis C. Accordingly, in the supported portion 45, the cross-sectional area substantially perpendicular to the longitudinal direction becomes a cross-sectional area S3 which is less than the maximum cross-sectional area S2. Thus, a step (step horn) 43 is formed between the maximum-diameter portion 42 and the supported portion 45. FIG. 3 is a view illustrating a cross section substantially perpendicular to the longitudinal direction in the supported portion 45. As illustrated in FIG. 3, in the supported portion 45, the cross-sectional shape substantially perpendicular to the longitudinal direction is formed in a different shape, which is different from a circular shape (perfect circular shape). Note that in this embodiment, although the cross-sectional shape substantially perpendicular to the longitudinal direction in the supported portion 45 is a hexagonal shape, this cross-sectional shape may be a polygonal shape such as a rectangular shape or a pentagonal shape, or an elliptical shape, if the cross-sectional shape is a different shape which is different from the circular shape.

An annular liner member 47 is attached to the supported portion 45. The liner member 47 is formed of an elastic material such as rubber. The liner member 47 abuts on the supported portion 45 from the outer peripheral side in a range from the proximal end to distal end of the groove formed in the supported portion 45 in the longitudinal direction, and abuts on the supported portion 45 over the entire circumference around the longitudinal axis C. In addition, the shaft portion 7 abuts on the liner member 47 from the outer peripheral side. The shaft portion 7 supports the vibration transmitting member 16 via the liner member 47, and keeps a state in which the shaft portion 7 and vibration transmitting member 16 are out of contact. Specifically, the vibration transmitting member 16 is supported relative to the housing 6 at the supported portion 45.

A projection portion 48, which projects toward the outer peripheral side with respect to the supported portion 45, is continuous on the distal side of the supported portion 45. In the projection portion 48, the outside diameter becomes the maximum outside diameter, and the cross-sectional area substantially perpendicular to the longitudinal direction becomes the maximum cross-sectional area S2. In addition, a horn 46 is provided on the distal side with respect to the projection portion 48. In the horn 46, the cross-sectional area substantially perpendicular to the longitudinal direction gradually decreases from the proximal side toward the distal side. However, even at the proximal end of the horn 46, the cross-sectional area substantially perpendicular to the longitudinal direction is less than the maximum cross-sectional area S2. In addition, in that part of the vibration transmitting member 16, which is located on the distal side with respect to the horn 46, the outside diameter is less than the maximum outside diameter and the cross-sectional area substantially perpendicular to the longitudinal direction is less than the maximum cross-sectional area S2 over the entire length in the longitudinal direction. Furthermore, in that part of the vibration transmitting member 16, which is located on the distal side with respect to the supported portion 45, the outside diameter is equal to or less than the maximum outside diameter and the cross-sectional area substantially perpendicular to the longitudinal direction is equal to or less than the maximum cross-sectional area S2 over the entire length in the longitudinal direction.

In the state in which the vibrating body unit 10 (vibration transmitting member 16) vibrates at any one of resonance frequencies in the predetermined frequency range, any of the vibration anti-nodes Ai is located apart from each of the step 43 and horn 46. Thus, in each of the step 43 and horn 46, the amplitude of ultrasonic vibration is increased. In addition, in the state in which the vibrating body unit 10 vibrates at any one of resonance frequencies in the predetermined frequency range, a vibration node N1, which is one of the vibration nodes Nj, is located in the supported portion 45.

Thus, it is possible to effectively prevent ultrasonic vibration from being transmitted from the vibration transmitting member 16 to the shaft portion 7 through the liner member 47.

Besides, in the state in which the vibrating body unit vibrates at any one of resonance frequencies in the predetermined frequency range, the vibration node (reference vibration node) N1, which occurs in the supported portion 45, is located most proximally among the vibration nodes (in this embodiment, Nj other than N0) occurring on the distal side with respect to the abutment surface (connection portion) 31B. Moreover, a vibration anti-node A1, which is apart from the vibration node (reference vibration node) N1 located in the supported portion 45 by a ¼ wavelength toward the proximal side, is located in the ultrasonic transducer 23. Specifically, the vibration anti-node A1 is located on the proximal side with respect to the abutment surface 31B (connection position B0). Accordingly, in the state in which the vibrating body unit 10 vibrates at any one of resonance frequencies in the predetermined frequency range, a dimension L2 between the vibration node (reference vibration node) N1 located in the supported portion 45 and the connection position (connection portion) B0 in the longitudinal direction is less than the ¼ wavelength from the vibration node (reference vibration node) N1 located in the supported portion 45 toward the proximal side.

In the state in which the vibrating body unit 10 vibrates at any one of resonance frequencies in the predetermined frequency range, the dimension L2 between the vibration node N1 and the connection position (connection) B0 in the longitudinal direction is four times or more greater than a dimension L1 between the vibration anti-node A1 and connection position (connection portion) B0 in the longitudinal direction. Accordingly, the dimension L1 between the vibration anti-node A1 and connection position (connection portion) B0 in the longitudinal direction is a ¹⁄₂₀ wavelength or less from the vibration anti-node A1 toward the distal side. Note that in this embodiment, the vibration anti-node A1 is located most distally among the vibration anti-nodes (A0, A1) occurring in the ultrasonic transducer 23, and is located closest to the connection position BO among the vibration anti-nodes Ai.

In the state in which the vibrating body unit 10 vibrates at any one of resonance frequencies in the predetermined frequency range, the dimension between the vibration node Ni located in the supported portion 45 and the distal end of the vibration transmitting member 16 in the longitudinal direction is a ¼ wavelength or more from the vibration node N1 located in the supported portion 45 toward the distal side. In this embodiment, the dimension in the longitudinal direction from a vibration anti-node A2, which is apart from the vibration node N1 located in the supported portion 45 by the ¼ wavelength toward the distal side, to the distal end of the vibration transmitting member 16 is substantially equal to any of integral multiples of a half-wave length. However, in this embodiment, the vibration anti-node A2, which is apart from the vibration node Ni by the ¼ wavelength toward the distal side, is located on the distal side with respect to the distal end of the horn 46. Because of the above-described configuration, in the state in which the vibrating body unit 10 vibrates at any one of resonance frequencies in the predetermined frequency range, a shape between the vibration node N1 located in the support portion 45 and the abutment surface 31B (connection position B0) in the longitudinal direction is asymmetric to a shape of a ¼ wavelength portion from the vibration node N1 toward the distal side.

Next, the function and advantageous effects of the vibration transmitting member 16 of the present embodiment will be described. In the present embodiment, ultrasonic vibration generated by the ultrasonic transducer 23 is transmitted to the energy applying portion 17, and thereby the vibrating body unit 10 including the vibration transmitting member 16 vibrates at any one of the resonance frequencies in the predetermined frequency range. At this time, any of the vibration anti-nodes Ai is located apart from the connection position B0 (the abutment surface (connection portion) 31B of the vibration transmitting member 16) between the ultrasonic transducer 23 and vibration transmitting member 16. In addition, in this embodiment, the vibration anti-node A1, which is located most distally among the vibration anti-nodes (A0, A1) occurring in the ultrasonic transducer 23, is located on the proximal side with respect to the connection position B0, and is located closest to the connection position B0 among the vibration anti-nodes Ai. In the state in which the vibrating body unit 10 vibrates at any one of resonance frequencies in the predetermined frequency range, none of the vibration anti-nodes Ai is located at or near the distal surface 31A of the ultrasonic transducer 23. Thus, the ultrasonic transducer 23, to which the vibration transmitting member 16 is not connected, does not vibrate as a single piece at any of the resonance frequencies in the predetermined range. Therefore, even if electric energy is supplied from the energy control device 5 to the ultrasonic transducer 23 to which the vibration transmitting member 16 is not connected, the ultrasonic transducer 23 is effectively prevented from vibrating as a single piece.

In addition, the length of the ¼ wavelength toward the distal side from the vibration anti-node A1, which is located most distally among the vibration anti-nodes (A0, A1) occurring in the ultrasonic transducer 23, varies in accordance with the cross-sectional area substantially perpendicular to the longitudinal direction of the vibration transmitting member 16 between the connection position BO and supported portion 45. For example, in one comparative example, in the vibration transmitting member (16), from the connection position (B0) to the proximal end of the supported portion (45), the cross-sectional area substantially perpendicular to the longitudinal direction is substantially uniform at the cross-sectional area S1 which corresponds to the cross-sectional area at the proximal end of the taper portion 41 of the present embodiment. In this case, compared to the present embodiment, the ¼ wavelength toward the distal side from the vibration anti-node A1, which is located most distally among the vibration anti-nodes (A0, A1) occurring in the ultrasonic transducer 23, becomes shorter, and a vibration node (N'1 (indicated by a dot-and-dash line in FIG. 2)), which is located apart from the vibration anti-node A1 by the ¼ wavelength toward the distal side, is located more proximally than the vibration node N1 of the present embodiment.

On the other hand, in the present embodiment, in the taper portion 41, the cross-sectional area substantially perpendicular to the longitudinal direction is increased from the cross-sectional area S1 to the maximum cross-sectional area S2. Thus, an average value of the cross-sectional area substantially perpendicular to the longitudinal direction of the vibration transmitting member 16 between the connection position BO and supported portion 45 becomes greater than in the above-described comparative example or the like. Accordingly, the ¼ wavelength toward the distal side from the vibration anti-node A1, which is located most distally among the vibration anti-nodes (A0, A1) occurring in the ultrasonic transducer 23, becomes greater, and the vibration node N1, which is located apart from the vibration anti-node A1 by the ¼ wavelength toward the distal side, is located more distally than the vibration node N'1 of the comparative example. Specifically, the distance between the vibration node N1, which is closest to the connection position B0 among the vibration nodes Nj, and the connection position B0 becomes greater.

Here, in the state in which the vibrating body unit 10 vibrates at any one of resonance frequencies in the predetermined frequency range, the stress due to ultrasonic vibration becomes zero at the vibration anti-node Ai, and the stress due to ultrasonic vibration becomes locally maximum at the vibration node Nj. Thus, in the ¼ wavelength portion between the vibration anti-node A1 and vibration node N1, the stress due to ultrasonic vibration becomes smaller away from the vibration node N1. In the present embodiment, as described above, since the distance between the vibration node N1 and connection position B0 is large, the stress occurring at the connection position B0 is small. Thus, the loss of vibration energy of ultrasonic vibration at the connection position B0 is suppressed, and the ultrasonic vibration is properly transmitted to the energy applying portion 17. Thereby, the vibration of the vibrating body unit 10 is stabilized, and the treated target is properly treated by the energy applying portion 17 by using the ultrasonic vibration.

In addition, in this embodiment, the maximum-diameter portion 42 is continuous from the distal end of the taper portion 41 to the proximal end of the supported portion 45. In the maximum-diameter portion 42, the cross-sectional area substantially perpendicular to the longitudinal direction of the vibration transmitting member 16 becomes the maximum cross-sectional area S2. Thus, the average value of the cross-sectional area substantially perpendicular to the longitudinal direction of the vibration transmitting member 16 between the connection position B0 and supported portion 45 becomes still greater, and the ¼ wavelength from the vibration anti-node A1 toward the distal side becomes still greater. Accordingly, the distance between the vibration node N1, which is closest to the connection position B0 among the vibration nodes Nj, and the connection position B0 becomes still greater, and the stress occurring at the connection position B0 is suppressed to be still smaller.

The configuration of the present embodiment, in which the taper portion 41 and maximum-diameter portion 42 are provided as described above, is particularly effective when the end effector 8 is reduced in size and the outside diameter (the cross-sectional area substantially perpendicular to the longitudinal direction) needs to be decreased over the entire length in the longitudinal direction in the vibration transmitting member 16. As described above, in the present embodiment, the vibration transmitting member 16, which prevents vibration of the ultrasonic transducer 23 as a single piece and reduces the loss of vibration energy at the connection position B0 between the vibration transmitting member 16 and the ultrasonic transducer 23, is provided.

Besides, in the present embodiment, the vibration transmitting member 16 is formed from a member having an outside diameter which is substantially equal to the maximum outside diameter, and having a cross-sectional area substantially perpendicular to the longitudinal direction, which is substantially equal to the maximum cross-sectional area S2. In this case, a part, such as the maximum-diameter portion 42, whose outside diameter becomes the maximum outside diameter, is formed without cutting the base material. In addition, a part, whose outside diameter becomes less than the maximum outside diameter, is formed by cutting the base material. The vibration transmitting member 16 is easily formed, as described above.

(Modifications)

In the above-described embodiment, etc., the handle 12 is located on the distal side with respect to the grip 11, and the handle 12 moves substantially parallel to the longitudinal direction in each of the opening motion and closing motion, but the embodiment, etc. are not limited to this. For example, in one modification, the handle 12 may be located on the proximal side with respect to the grip 11. In another modification, the handle 12 may move in a direction crossing the longitudinal direction in each of the opening motion and closing motion. In still another modification, the rotation knob 21 may not be provided.

Besides, in addition to the ultrasonic vibration, other treatment energy may be supplied to the end effector 8. For example, in one modification, ultrasonic vibration is transmitted to the energy applying portion 17, and high-frequency electric energy is supplied to the energy applying portion 17 and grasping member 18. In this case, a high-frequency current is passed between the energy applying portion 17 and grasping member 18 through a grasped treated target.

Additionally, in the above-described embodiment, etc., in the state in which the vibrating body unit 10 vibrates at any one of resonance frequencies in the predetermined frequency range, the dimension of the ultrasonic transducer 23 in the longitudinal direction is greater than the half-wave length from the proximal end of the ultrasonic transducer 23, and is less than a ¾ wavelength from the proximal end of the ultrasonic transducer 23, but the embodiment, etc. are not limited to this. For example, in one modification, the dimension of the ultrasonic transducer in the longitudinal direction may be greater than 1 wavelength from the proximal end of the ultrasonic transducer 23, and may be is less than a 5/4 wavelength from the proximal end of the ultrasonic transducer 23. Specifically, in the state in which the vibrating body unit 10 vibrates at any one of resonance frequencies in the predetermined frequency range, it should suffice if any one (e.g. N1) of the vibration nodes Nj is located in the supported portion 45 of the vibration transmitting member 16, and the vibration anti-node (e.g. A1), which is apart from the vibration node (e.g. N1) located in the supported portion 45 by the ¼ wavelength toward the proximal side, is located in the ultrasonic transducer 23. In this case, the vibration anti-node (e.g. A1), which is apart from the vibration node (e.g. N1) located in the supported portion 45 by the ¼ wavelength toward the proximal side, is closest to the connection position (the connection portion of the vibration transmitting member 16) B0 among the vibration anti-nodes Ai.

Additionally, in the above-described embodiment, etc., in the state in which the vibrating body unit 10 vibrates at any one of resonance frequencies in the predetermined frequency range, the dimension in the longitudinal direction between vibration node (e.g. N1) located in the supported portion 45 and the distal end of the vibration transmitting member 16 is greater than the ¼ wavelength toward the distal side from the vibration node (e.g. N1) located in the supported portion 45, but the embodiment, etc. are not limited to this. In one modification, the dimension in the longitudinal direction between vibration node (e.g. N1) located in the supported portion 45 and the distal end of the vibration transmitting member 16 may be substantially equal to the ¼ wavelength toward the distal side from the vibration node N1 located in the supported portion 45. In this case, the vibration anti-node (e.g. A2), which is apart from the vibration node (e.g. N1) located in the supported portion 45 by the ¼ wavelength toward the distal side, is located at the distal end of the vibration transmitting member 16.

Additionally, in one modification, the end effector 8 may not be provided with the grasping member 18. In this case, none of the grip 11, handle 12 and movable portion 15 is provided, and the energy applying portion 17 has a hook shape, a spatula shape or a curette shape. In this modification, in the state in which the energy applying portion 17 is put in contact with the treated target, ultrasonic vibration is transmitted to the energy applying portion 17 (end effector 8). Then, by applying the transmitted ultrasonic vibration, the treated target is treated by using the ultrasonic vibration. In this case, too, in addition to the ultrasonic vibration, other treatment energy may be supplied to the energy applying portion 17.

In the above-described embodiment, etc., the vibration transmitting member (16) is attached to the ultrasonic transducer (23), and transmits ultrasonic vibration, which is generated by the ultrasonic transducer (23), from the proximal side toward the distal side, thereby vibrating at a resonance frequency in a predetermined frequency range. The vibration transmitting member (16) includes the connection portion (31B) which is connected to the ultrasonic transducer (23). When a reference vibration node (e.g. N1) which is located most proximally among the vibration nodes (e.g. Nj other than N0) occurring on the distal side with respect to the connection portion (31B), is defined, in the state in which the vibration transmitting member (16) vibrates at the resonance frequency in the predetermined frequency range, the taper portion (41) is provided in the vibration transmitting member (16) between the connection portion (31B) and the reference vibration node (N1) in the longitudinal direction. In the taper portion (41), the cross-sectional area substantially perpendicular to the longitudinal direction gradually decreases from the distal side toward the proximal side.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A vibration transmitting member attached to an ultrasonic transducer, the vibration transmitting member being configured to transmit ultrasonic vibration, which is generated by the ultrasonic transducer, from a proximal side toward a distal side, thereby vibrating at a resonance frequency in a predetermined frequency range, the vibration transmitting member comprising:
   a connection connected to the ultrasonic transducer; and
   a cross-sectional area decreasing part provided between the connection and a reference vibration node in a longitudinal direction, the reference vibration node being defined as being located most proximally among vibration nodes occurring on the distal side with respect to the connection in a state in which the vibration transmitting member vibrates at the resonance frequency, the cross-sectional area decreasing part having such a cross-sectional area perpendicular to the longitudinal direction as to gradually decrease from the distal side toward the proximal side.

2. The vibration transmitting member of claim 1, wherein in the state in which the vibration transmitting member vibrates at the resonance frequency in the predetermined frequency range, a dimension between the reference vibration node and the connection in the longitudinal direction is less than a ¼ wavelength from the reference vibration node toward the proximal side.

3. The vibration transmitting member of claim 2, wherein in the state in which the vibration transmitting member vibrates at the resonance frequency in the predetermined frequency range, a shape between the reference vibration node and the connection in the longitudinal direction is asymmetric to a shape of a ¼ wavelength portion from the reference vibration node toward the distal side.

4. The vibration transmitting member of claim 1, wherein the vibration transmitting member extends through an inside of a housing, and
   the vibration transmitting member is supported relative to the housing, the vibration transmitting member further including a supported portion in which the reference vibration node is located in the state in which the vibration transmitting member vibrates at the resonance frequency.

5. The vibration transmitting member of claim 4, further comprising a maximum-diameter portion which is provided between the supported portion and the cross-sectional area decreasing part in the longitudinal direction, an outside diameter becoming a maximum outside diameter and the cross-sectional area perpendicular to the longitudinal direction becoming a maximum cross-sectional area in the maximum-diameter portion,
   wherein in a part on the distal side with respect to the supported portion, the outside diameter becomes the maximum outside diameter or less, and the cross-sectional area perpendicular to the longitudinal direction becomes the maximum cross-sectional area or less.

6. The vibration transmitting member of claim 4, wherein in the supported portion, the cross-sectional area perpendicular to the longitudinal direction has a different shape which is different from a circular shape.

7. An ultrasonic treatment instrument comprising:
   the vibration transmitting member of claim 1; and
   a housing which is capable of being held, the vibration transmitting member extending from an inside of the housing toward the distal side, and the ultrasonic transducer being attached to the vibration transmitting member in the inside of the housing.

8. The ultrasonic treatment instrument of claim 7, wherein the vibration transmitting member is supported relative to the housing, the vibration transmitting member including a supported portion in which the reference vibration node is located in the state in which the vibration transmitting member vibrates at the resonance frequency, and
   the ultrasonic treatment instrument further includes:
   a liner member formed of an elastic material, and attached to the supported portion from an outer peripheral side; and
   a shaft which is attached to the housing from the distal side, and through which the vibration transmitting member is inserted, the vibration transmitting member extending through an inside of the shaft, and the shaft supporting the vibration transmitting member via the liner member.

9. A vibrating body unit comprising:
   the vibration transmitting member of claim 1; and
   an ultrasonic transducer configured to generate the ultrasonic vibration which is transmitted to the vibration transmitting member.

10. The vibrating body unit of claim 9, wherein in the state in which the vibration transmitting member vibrates at the resonance frequency in the predetermined frequency range, a vibration anti-node, which is located apart from the reference vibration node by a ¼ wavelength toward the proximal side, is located in the ultrasonic transducer.

* * * * *